United States Patent [19]

Henry

[11] 4,182,106
[45] Jan. 8, 1980

[54] ELASTICALLY DEFORMABLE WIRE

[75] Inventor: Michael E. Henry, Long Beach, Calif.

[73] Assignee: Cablestrand, Long Beach, Calif.

[21] Appl. No.: 922,188

[22] Filed: Jul. 5, 1978

[51] Int. Cl.² .......................... D07B 1/00; D02G 3/12; D02G 3/44; A61C 7/00

[52] U.S. Cl. .................................. 57/212; 57/311; 433/20

[58] Field of Search .................. 57/3, 6, 9, 13, 14, 57/15, 139, 144, 145, 160, 161, 166, 210, 212, 213, 215, 311, 58.3–58.38, 59; 32/14 R, 14 A, 14 E

[56] References Cited

U.S. PATENT DOCUMENTS

| | | | |
|---|---|---|---|
| 251,114 | 12/1881 | Hallidie | 57/212 X |
| 592,453 | 10/1897 | Sisum | 57/59 X |
| 1,961,379 | 6/1934 | Morgan | 57/14 X |
| 2,353,432 | 7/1944 | Arrington | 57/59 X |
| 3,052,081 | 9/1962 | Wallshein | 57/311 X |
| 3,395,528 | 8/1968 | Lucht | 57/212 |
| 3,566,596 | 3/1971 | Penncuick et al. | 57/166 X |
| 3,729,824 | 5/1973 | Baues et al. | 32/14 A |
| 3,878,609 | 4/1975 | Wallshein | 32/14 A |
| 3,902,307 | 9/1975 | Schoerner | 57/58.36 X |
| 3,997,970 | 12/1976 | Hodgson | 32/14 R |
| 4,086,702 | 5/1978 | Wallshein | 32/14 A |

Primary Examiner—Donald Watkins
Attorney, Agent, or Firm—Fulwider, Patton, Rieber, Lee & Utecht

[57] ABSTRACT

A wire construction is provided in which five fine filaments of stainless steel wire are helically overwound about a center filament, also formed of stainless steel. The diameter of the central filament is slightly larger than the diameter of the helically wound filaments, which are of uniform diameter. The wire so constructed retains a high degree of elasticity following manufacture, and is especially suitable for application as an orthodontic wire for use in bracework for straightening teeth, especially the teeth of adolescent children. The wire is formed on a multi-bobbin tubular strander, and during manufacture all of the wire strands are maintained under tension, although the center strand is maintained under greater tension than the helically overwound filaments.

13 Claims, 7 Drawing Figures

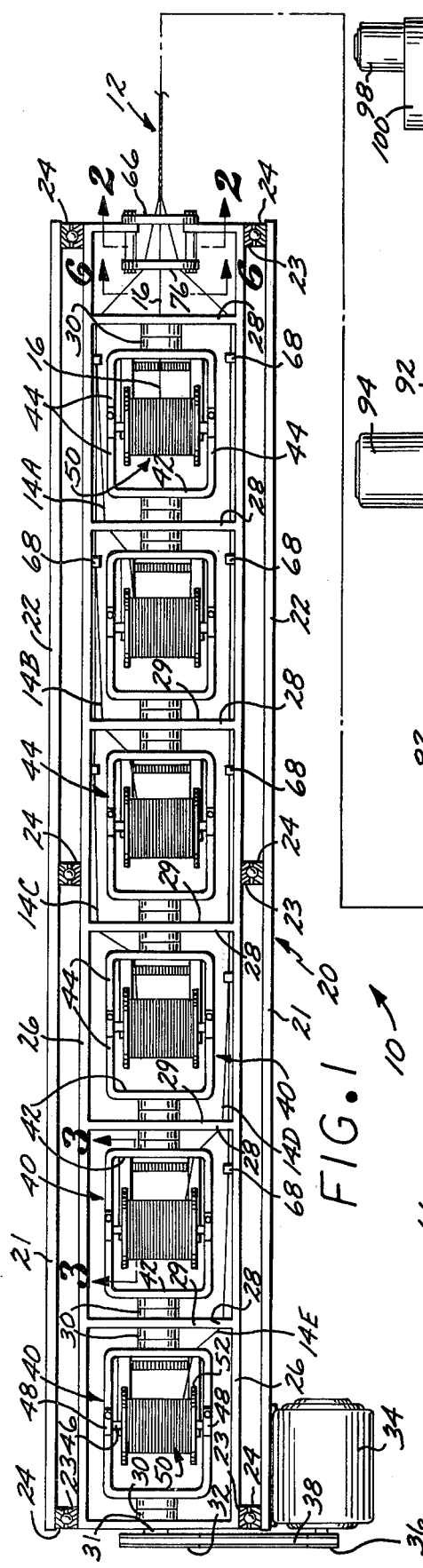
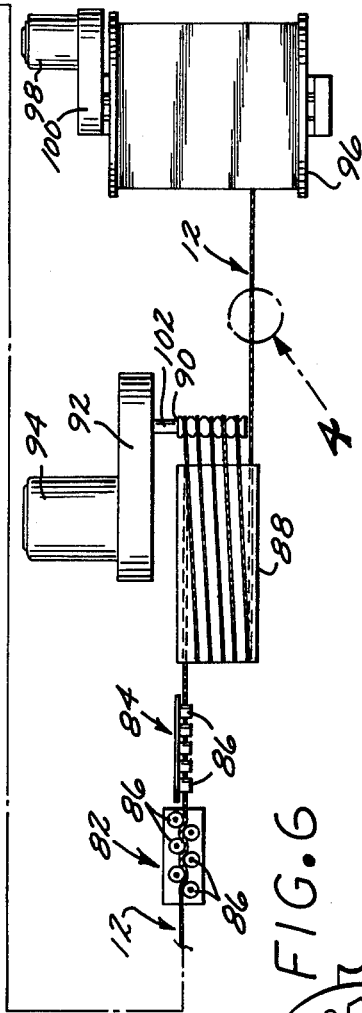
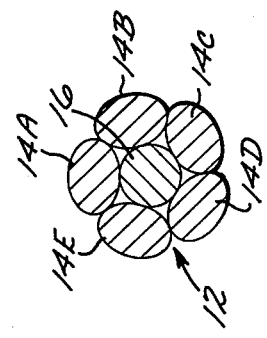
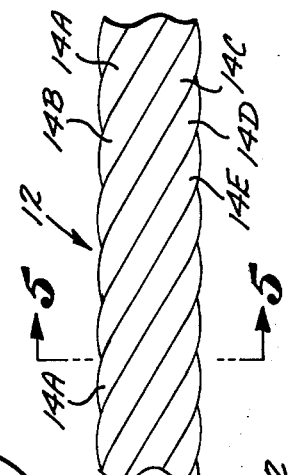
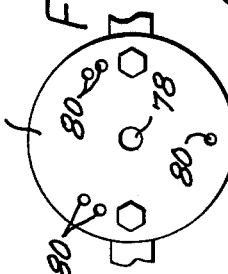
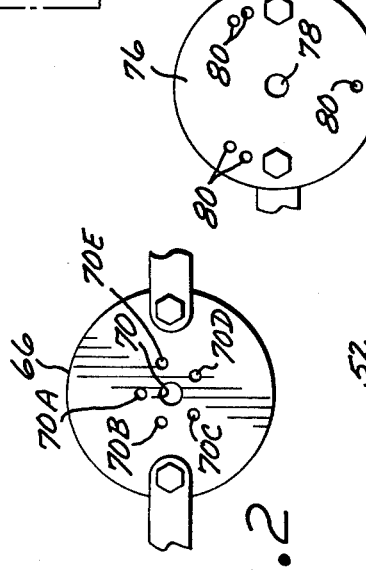
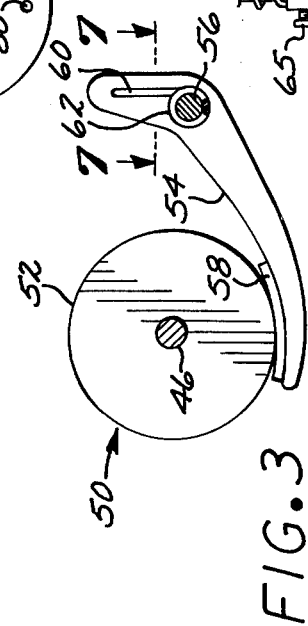

ELASTICALLY DEFORMABLE WIRE

FIELD OF THE INVENTION

The present invention relates to high strength fine wire constructions, and methods of manufacturing such wires.

BACKGROUND OF THE INVENTION

In the past, various types of fine, high strength wire configurations have been evolved. One use for such wires is in the construction of orthodontic bracework, where the wire is bent into a U-shaped configuration to conform to the jaw line of an orthodontic patient, and used to train teeth into straightened alignment. Very frequently, especially during adolescent and pre-adolescent years, childrens teeth, for one reason or another, tend to emerge from the gum line other than in proper alignment. For both cosmetic and medical reasons, it is quite desirable to change the pattern of alignment of such teeth so that they do not become permanently set in misalignment in adulthood. Straightening of teeth, or "training" as it is sometimes called, is typically achieved by providing each tooth with a plastic collar or harness which contains narrow spacers that project between adjacent teeth. Each tooth harness also includes a small ring projecting outward from the tooth with which it is associated to accomodate passage of a training wire or brace so that the tooth is forced into proper alignment.

It is highly desirable for the training wire used in orthodontic bracework to be quite strong, as it is always under tension, but yet to also be elastic so that it tends to return to a straightened configuration from the U-shaped pattern into which it is deformed and thereby exert a straightening force on the teeth. Numerous conventional wire structures have been designed for this purpose, but all have heretofore suffered from certain deficiencies. Many such wire constructions are too brittle, and tend to break too frequently. Each time the orthodontic training wire breaks, the patient much have a replacement wire installed by an orthodontist. This is extremely time consuming, both for the patient and the orthodontist, and contributes greatly to the expense of orthodontic bracework.

Other conventional orthodontic wire constructions lose their elasticity with time, and hence cease to perform their intended function of straightening the teeth. These training wires must likewise be replaced with some frequency, which similarly contributes considerably to the expense of orthodontic bracework. Typically, conventional orthodontic training wire constructions exhibit only about a 25% degree of elasticity when laterally deformed into a U-shaped configuration, as is necessary in the installation of dental bracework. The improved orthodontic wire of the present invention exhibits about a 40% return toward linearity when released, even after prolonged use.

SUMMARY OF THE INVENTION

Heretofore, manufacturers of orthodontic training wire have attempted to produce wire by helically overwinding a plurality of filaments about a center filament to produce a wound orthodontic training wire. Always, prior attempts have been limited by the constraint of utilizing at least six filaments helically overwound about a central filament in the training wire construction. This has been considered as a logical constraint, since the minimum number of strands, or filaments, of circular cross section which can be positioned about and encompass a central strand of equal or greater diameter and still remain in tangential contact with strands adjacent to it is six. That is, when six strands of equal diameter are positioned about a central strand of the same diameter, the central strand is completely enclosed within the confines of the outer strands and is contact with each of them, and the outer strands are tangent to each other. However, it has been found, according to the present invention, that overwinding five strands of uniform diameter helically about a central strand of greater diameter produces a superior orthodontic wire. A wire construction, according to the present invention, is of much greater durability and lateral elasticity than conventional orthodontic training wires.

In the wire of the present invention, the five outer wire filaments are overwound helically along the length of a central filament under considerable longitudinal tension. The central wire is maintained under even greater tension. The resulting structure produced causes the outer wires to depart slightly from a circular configuration, and to assume a somewhat oblate or oval configuration so that they are tangent to each other, while still remaining tangent to the central wire. This wire construction produce a highly superior orthodontic training wire.

The present invention of a wire construction, and its method of manufacture, are more clearly illustrated with reference to the accompanying drawings.

DESCRIPTION OF THE DRAWINGS

FIG. 1 is a plan view of a multiple bobbin tubular stranding machine for forming the wire of the invention.

FIG. 2 is a sectional view taken along the lines 2—2 of FIG. 1.

FIG. 3 is a sectional view taken along the lines 3—3 of FIG. 1.

FIG. 4 is a detail of the wire construction taken at location 4 in FIG. 1.

FIG. 5 is a cross sectional detail of the wire construction of FIG. 4.

FIG. 6 is a sectional view taken along the lines 6—6 of FIG. 1.

FIG. 7 is a plan view of the brake mechanism mounting shaft taken along the lines 7—7 of FIG. 3.

DESCRIPTION OF THE EMBODIMENT AND IMPLEMENTATION

With reference to FIG. 1, a six bobbin tubular stranding machine is depicted generally at 10. As a practical matter, and because of the prior art constraints heretofore existing, a six bobbin machine is not commercially available, and instead a seven bobbin tubular strander manufactured by the Synchro Machine Company, of Raway, New Jersey, Model PC-4A29-USRL has been utilized in the manufacture of the wire of the invention. The commercially available machine differs from the device depicted in FIG. 1 only in that an additional longitudinally disposed bobbin creel is employed. When a seven bobbin tubular strander is employed to practice the method, and create the wire construction of the present invention, the extra bobbin creel is left empty.

The wire produced according to the invention is designated at 12 in FIGS. 4 and 5. Preferably, the wire 12 is of generally circular cross section of no greater than about 0.025 inches in diameter. The wire 12 is constructed with five different strands or filaments 14A through 14E helically disposed in wound arrangement about a center filament 16, visible in cross section in FIG. 5. The center filaments 16 is of a circular cross sectional area larger than the cross section area of each of the surrounding filaments 14A through 14E. The cross section of each of the overwound filaments 14A through 14E in any event appears eliptical in FIG. 5 because of the helical winding angle. Nevertheless, while the filaments 14A through 14E are originally of circular diameter, they are flattened slightly during the helical winding process, and assume a slightly oblate cross section, as reflected in FIG. 5, with their minor axes radially aligned relative to the central circular filament 16, and with their major axes generally parallel to tangents of the helically overwound filaments 14A through 14E with the central filament 16. It can be seen that the helically overwound filaments 14A through 14E contact each other in general tangential arrangement at their surfaces near their extremities along their major axes. The helically overwound filaments 14A through 14E thereby completely radially encapsulate the central filament 16.

It should be noted that although the wire filaments 14A through 14E and 16 are indicated as being exactly tangent to each other in FIG. 5, because of the high longitudinal tensile stress placed on all of the filaments during winding, the filaments are flattened slightly at their contact interfaces. Hence the outer perimeters of the filaments, when viewed in cross section, are not precisely continuous curves.

As is apparent in FIG. 4, the helical angle of disposition of the surrounding filaments is about 62°, although it may easily vary between about 60° and 65° relative to a transverse plane through the wire 12.

Preferably, the filaments 14A through 14E and 16 are all formed of high tensile strength stainless steel, preferably number 302-304. The filaments all have a rated strength of from at least 340,000 to 415,000 kilograms per square inch.

The tubular strander 10 used to form the wire 12 is a device about 20 feet long and includes a generally cylindrical framework 20 which is divided longitudinally in half into two segments, 21 and 22 lying on either side of a vertical plane. Each of the segments 21 and 22 includes a semicylindrical wire mesh guard cover over the top half thereof which is hingably attached along one edge so that it can be opened to allow access for servicing and replenishment of filament supplies. The semicylindrical wire mesh guard covers are omitted from the illustration of FIG. 1 to allow clear visibility of the operating mechanism of the tubular strander 10.

The framework 20 includes heavy steel, circular brackets 23 mounted in vertical planes which extend over the top and underneath the operating mechanism of the tubular strander 10 at intervals therealong and which are bolted to upright steel standards 24 to carry the strander mechanism in longitudinal suspension above the work area floor. The framework 20 also includes horizontal elongated steel struts 26 extending the length of the cylindrical body of the strander 10 and spaced from each other at arcuate intervals about the perimeter thereof. The struts 26 are of arcuate cross section and are welded to the semicircular brackets 23 at the radially interior surfaces thereof. Circular steel bands 28 are spaced at periodic intervals along the struts 26 and are welded thereto in transverse orientation. The bands 28 form the rims of circular disk shaped partition plates 29 that extend transversely across the tubular strander 10 and separate the operating the mechanism thereof into bobbin compartments. These plates 29 include central apertures therein to allow axial interconnection of disk shaped bobbin creel couplings 30.

The end-most bobbin creel coupling 30 includes a rearwardly extending shaft 31 connected to a chain driven sprocket 32. A 7½ horsepower ball bearing type motor 34 rotates a drive sprocket 36 at a high speed. Torque is transferred to the strander sprocket 32 by means of a drive chain 38 to drive the strander at 1850 rpm. The motor casing 34 is bolted to a mounting which is welded to the frame 20 to minimize whipping of the chain 38.

A creel 40 is carried between each pair of creel couplings 30 in the bobbin compartments defined between adjacent partition plates 29. Each creel 40 includes a transverse coupling plate 42 from which longitudinally directed arms 44 reach toward the center of the bobbin cavity, where they meet opposing arms 44 extending from the mating coupling plate 42 attached to the other coupling 30 associated with the creel. Where the opposing arms 44 meet, a recess is defined to carry a bobbin axle 46. Brackets 48 entrap each axle 46 relative to the creel arms 44.

A bobbin spool 50 is rotatably mounted upon each bobbin axle 46 and is located within each creel 40 and carries a supply of one of the filaments 14A through 14E or 16 wound thereon. The filaments 14A through 14E and 16 are wound on the bobbin spools 50 and are drawn therefrom as the spools 50 rotate about the axles 46. The filaments on each bobbin are confined between spool end disk plates 52. All of the creels 40 are driven synchronously by the motor 34 to rotate about the longitudinal axis of the strander 10.

A braking mechanism, one of which is depicted in FIG. 3, is adjusted to exert an appropriate drag on the rotation of each of the bobbin spools 50 about axle 46 within creels 40. Each braking mechanism includes a pair of longitudinally disposed bell cranks 54 mounted for rotation about a transverse brake shaft 56 carried within each creel 40 and extending between opposing ones of the creel arms 44. The remote end of the longest arm of each bell crank 54 has a brake shoe 58 which rides in contact with the perimeter of the associated bobbin retaining disk 52. Such a brake arm mechanism according to FIG. 3 exists on either side of each bobbin 50 so that rotation of each of the spool end disk plates 52 is retarded by a brake shoe 58 riding in contact therewith.

The force with which the bell crank 54 presses the brake shoe 58 against a rotating spool end disk plate 52 is governed by the biasing force exerted by the end 60 of the coil spring 62 which is connected to the short arm of the bell crank 54. The end 60 of each coil spring 62 passes into an aperture in the short arm of the bell crank 54 and the coils of the spring 62 extend helically about the shaft 56 toward its center, as illustrated in FIG. 7. At the center, each coil spring 62 terminates in a connection to a sleeve 64, which is positioned at a rotational disposition relative to the shaft 56 by a set screw 65. To increase the braking force applied by the brake shoe 58, the sleeve 64 is rotated to tightened the windings of the coils of the spring 62, and thus exert increased force on the bell crank 54. Since the springs 62 on either side of each bobbin 50 are oppositely wound about the shaft 56, rotation of the collar 64 in one direction increases or reduces the spring force applied by both of the brake shoes 58 associated with a particular bobbin 50.

The force applied by the brake shoes 58 on each of the bobbins 50 is adjusted depending upon how much each spool weighs, the amount of friction on each bobbin shaft 46 and the longitudinal position of the bobbin 50 along the length of the strander 10. Adjustment is performed with respect to each of the bobbins 50 until the filaments 14A through 14E are wound in a helical pattern about the center filament 16, as depicted in FIG. 4.

The force applied by the brake shoe 58 in connection with the front bobbin carrying the filament 16 is much greater than the corresponding forces applied to any of the bobbins carrying the filaments 14A through 14E. The least braking force is applied to the bobbin 50 carrying the filament 14E, which is mounted furthest from the forming head 66, and each bobbin 50 located forwardly therefrom receives a greater braking force.

Each of the filaments 14A through 14E and 16 are drawn from their respective bobbins 50 and passed to funnel guides located near the perimeters of the disk shaped partition plates 29 immediately forward of the bobbin 50 from which the filament is drawn. The funnel shaped guides have an enlarged opening toward the bobbin 50 from which the filament passing therethrough is drawn so that the filament can be drawn smoothly and longitudinally toward the guide plate 76 through funnel guides 68 located forward in other bobbin compartments. The filament 16, on the other hand, is drawn directly through a funnel guide centrally located in the creel coupling 30 immediately forward therefrom, and is passed along the axis of rotation of the tubular strander 10 through the guide plate 76 and then axially through a forming head 66.

The structure of the guide plate 76 is depicted in detail in FIG. 5. The guide plate 76 is located at the forward end of the struts 26 and is attached thereto and carried in rotation. The guide plate 76 has apertures therein spaced in the configuration depicted in FIG. 6. The filament 16 passes through the central axial aperture 78, while the filaments 14A through 14E each travel through one of the periferal apertures 80.

The structure of the forming head 66 is depicted in detail in FIG. 2. The forming head 66 is bolted to the guide plate 76 at the forward end of the strander 10. The central filament 16 passes through the central aperture 70 located in forming head 66 while the filaments 14A through 14E pass through the apertures 70A through 70E located at equally spaced uniform radial distances from aperture 70. Preferably, the central aperture 70 is about 0.813 inches in diameter while the five peripheral apertures 70A through 70E are each about 0.187 inches in diameter and are spaced from the aperture 70 at a center to center distance of 1.06 inches.

As the motor 34 drives the creels 40 in rotation about the axis of the strander 10, the creel couplings 30 carry the disk shaped partitions 29 and the struts 26 in rotation. The guide plate 76 and the forming head 66 are also carried in rotation about the strander axis by the struts 26.

As the filaments emerge from the forming head 66, the filaments 14A through 14E are helically wound about the central filament 16 in the manner depicted in FIG. 1 and in the configuration depicted in FIG. 4 to form the wire 12 of the invention. The wire 12 is passed through a pair of wire straightners 82 and 84, longitudinally positioned along the path of travel of the wire 12 and oriented at right angles to each other as illustrated in FIG. 1. The wire straightners 82 and 84 each have a plurality of staggered rollers 86 located thereon between which the wire 12 travels and by which the wire 12 is straightened.

Once wound and straightened in the configuration of FIG. 4, the wire 12 is taken up on a large capstan 88 and passes to a smaller capstan 90.

The capstan 90 is much smaller than capstans normally used in the manufacture of orthodontic wire. The capstan 90 is about 2½" maximum diameter with a diameter of about 2⅛" from root to root of the grooves therein. The axial length of the capstan 90 is 2¾" and it is bored 1⅝" in diameter to receive a drive shaft 102. The capstan 90 has six grooves formed along its length.

The capstan 90 is driven by meshed spur gears located within a gear box 92 by an electric motor 94. The motor 94 drives a spur gear of either 20 or 23 teeth, and a gear of a larger number of teeth, drives the capstan 90. Gears of different ratio are used, depending upon the initial diameters of the filaments 16 and 14A through 14E. Together, the capstan 88 and 90 maintain the wire 12 and strands 14A through 14E and 16 under considerable tension. The wire 12 is passed in the pattern as indicated in FIG. 1, riding within corresponding grooves in the capstans 88 and 90. Upon leaving the final groove of the capstan 88, the wire 12 is passed to a take-up spool 96, which is driven by another motor 98 through gears in a gear box 100.

As previously noted, all of the outer filaments 14A through 14E of the wire 12 depicted in FIG. 5 are initially of a uniform circular diameter. Appropriate corresponding filament diameters of the filaments 16 and 14A through 14E are set forth in Table I, along with the corresponding number of teeth in the gears to be used in the gear box 92.

TABLE I

| Filament 14A-E Diameter | Filament 16 Diameter | Gear box 92- Gear Teeth |
| --- | --- | --- |
| .006" | .0065" | 97 by 23 |
| .0065 | .007 | 97 by 23 |
| .005 | .006 | 100 by 20 |
| .0045 | .005 | 97 by 23 |

To manufacture a helically wound wire for use in orthodontic braces, a filament selection is made from Table I. For example, the bobbin 50 closest to the guide plate 76 may contain a stainless steel filament number, 302-304 of rated strength of 340,000–415,000 kpsi (kilograms per square inch) and 0.0065 inches in diameter as the filament 16. The remaining bobbins 50 contain filaments of 0.006" in diameter, also of stainless steel and of an identical tensile strength rating. Motor 34 is powered to rotate the tubular stranding machine 10 at 1850 rpm, with all creels 40 rotating synchronously, along with the guide plate 76 and the forming head 66. The wire 12 is then formed by the filaments 14A–14E which are wound in a helical arrangement about the center filament 16, which of course is of cross sectional area larger than the cross sectonal area of each of the filaments 14A–14E. The filaments 14A–14E radially encapsulate the filament 16, as indicated in FIG. 5, to form the wire 12, depicted in detail in FIG. 4. Motors 94 and 98 are operated to maintain tension on the wire 12 and to take it up on the spool 96.

The braking mechanism of FIG. 3 associated with the creel 50 upon which the filament 16 is wound, is tightened as much as possible, but short of causing the tensile stress on the filament 16 to exceed its rated limit. A braking system according to FIG. 3 is likewise employed in association with each of the other creels 40, and a drag is applied to each of the bobbins 50 in the manner previously described. The more remote the bobbin from the forming head 66, the less is the brake drag applied thereto. The brake drag on the bobbin 50 furthest from the forming head 66 is less than on any other bobbin. The brake mechanisms according to FIG. 3 for each of the bobbins 50 is adjusted until a uniform helical winding of the filaments 14A–14E about the center strand 16 is produced, as in FIG. 4. Should adjacent windings of the filaments 14A–E tend to separate or to coil about each other, the brake drag on the bobbin 40 feeding the filaments involved is altered.

Once the steel wire 12 is taken up on the spool 96, it is ready for use. As previously noted, it has particular utility in connection with orthodontic braces, as its strength, durability and elastic memory from lateral deflection is superior to orthodontic wire heretofore available.

While the particular filament diameters indicated in Table I result in the production of a wire 12 which has the advantageous features noted, these particular filament sizes are not limiting. To the contrary, the stainless steel strands or filaments 16 and 14A–14E may vary from between about 0.004 and about 0.007 inches in initial diameter. Likewise, the construction of the capstan 90 is not necessarily of the dimensions and configuration suggested. It is sufficient if the capstan 90 is less than about 3" in diameter. Likewise, various other engineering changes, such as gear ratio, rotation speed, etc. may be varied without departing from the invention. Rather, the scope of the invention is defined in the claims appended hereto.

I claim:

1. A wire construction in which five filaments of equal cross sectional area are helically disposed in overwound arrangement about a single center filament of cross sectional area larger than the cross sectional area of each surrounding filament, wherein said filaments are all formed of stainless steel, and the ratio of diameter of the stock from which said center filament is formed to the diameter of each of said surrounding filaments is no greater than 1.2:1, and the helical angle of disposition of said surrounding filaments about said center filament is between about 60° and about 65°.

2. A wire construction according to claim 1 further characterized in that the ratio of diameter of the stock from which said center filament is formed to diameter of each of said surrounding filaments is at least 1.07:1.

3. A wire construction according to claim 1 further characterized in that said wire is of circular cross section of no greater than about 0.025 inches in diameter.

4. A wire construction according to claim 1 further characterized in that said filaments are metal strands having a tensile strength from about 340,000 kilograms per square inch to about 415,000 kilograms per square inch.

5. A method of making wire comprising winding five stainless steel filaments of uniform cross sectional area in helical engagement about a single center filament of cross sectional area larger than the cross sectional area of each of said five filaments at a helical angle of disposition of between about 60° and about 65° to radially encapsulate said center filament, and the ratio of diameter of the stock of which said center filament is formed to diameter of each of said surrounding filaments is no greater than 1.2:1.

6. The method according to claim 5 further comprising maintaining tension on said center filament to a greater extent than on said five surrounding filaments.

7. The method according to claim 6 further characterized in that said step of winding is performed on a tubular strander having at least six bobbins, wherein each of said filaments is taken from a separate bobbin, and said bobbins are axially displaced from each other and synchronously rotated together and said filaments are drawn from said bobbins through a forming head having a large central aperture to receive said center filament and five radially equidistant arcuately spaced small peripheral apertures to each receive one of said five surrounding filaments.

8. The method according to claim 7 further comprising selectively and individually exerting a drag on the release of each of said filaments from the bobbins from which they are drawn, and adjusting said drag to maintain formation of said wire in a uniform cross section.

9. The method according to claim 7 further comprising drawing on said wire as it is formed at said forming head and maintaining tension thereon by taking said wire up on a capstan that has a plurality of spaced grooves in its outer surface, and passing said wire onto a take-up reel.

10. The method according to claim 9 further characterized in that said filaments are stainless steel strands each between about 0.004 and about 0.007 inches in diameter and said capstan is less than about 3 inches in diameter.

11. The method according to claim 10 further characterized in that said filaments are drawn through a forming head having a central aperture about 0.813 inches in diameter and five peripheral apertures about 0.187 inches in diameter spaced equidistant about said central aperture at a center to center distance therefrom of about 1.06 inches.

12. The method according to claim 5 further characterized in that said filaments are metal strands having a tensile strength of between about 340,000 and 415,000 kilograms per square inch.

13. The method according to claim 12 further characterized in that said filaments are stainless steel.

* * * * *

UNITED STATES PATENT AND TRADEMARK OFFICE
CERTIFICATE OF CORRECTION

PATENT NO. : 4,182,106

DATED : January 8, 1980

INVENTOR(S) : Michael E. Henry

It is certified that error appears in the above-identified patent and that said Letters Patent are hereby corrected as shown below:

At column 3, line 39 delete the word "kilograms" and substitute in place there of the word --pounds--.

At column 6, lines 50-51, please delete "kpsi (kilograms" and substitute in place thereof --(pounds--.

At column 8, at lines 1,2 and 54, please delete the word "kilograms" and substitute in place thereof --pounds--.

Signed and Sealed this

Fifteenth Day of July 1980

[SEAL]

Attest:

SIDNEY A. DIAMOND

Attesting Officer

Commissioner of Patents and Trademarks